United States Patent [19]

Nosé et al.

[11] Patent Number: 5,080,796

[45] Date of Patent: * Jan. 14, 1992

[54] THERMOFILTRATION OF PLASMA

[75] Inventors: Yukihiko Nose', Cleveland Heights; Paul S. Malchesky, Painsville Township; Takashi Horiuchi, South Euclid, all of Ohio

[73] Assignee: The Cleveland Clinic Foundation, Cleveland, Ohio

[*] Notice: The portion of the term of this patent subsequent to Oct. 30, 2007 has been disclaimed.

[21] Appl. No.: 478,624

[22] Filed: Feb. 12, 1990

Related U.S. Application Data

[63] Continuation of Ser. No. 220,919, Jul. 18, 1988, Pat. No. 4,966,709, which is a continuation of Ser. No. 810,926, Dec. 19, 1985, abandoned.

[51] Int. Cl.⁵ .................. B01D 37/00; B01D 61/14
[52] U.S. Cl. .................. 210/651; 210/742; 210/774; 210/149; 210/175; 210/321.6; 210/434; 210/806; 210/905; 210/908; 604/5; 604/6; 604/113
[58] Field of Search .................. 604/4, 5, 6, 113, 114; 210/645, 649, 650, 651, 742, 774, 149, 175, 321.6, 434, 903, 905, 908, 806, 295

[56] References Cited

U.S. PATENT DOCUMENTS

| 4,181,609 | 1/1980 | Wardlaw et al. | 210/774 |
| 4,267,040 | 5/1981 | Schäl | 210/149 |
| 4,397,747 | 8/1983 | Ikeda | 210/651 |
| 4,424,132 | 1/1984 | Iriguchi | 210/800 |
| 4,966,709 | 10/1990 | Nosé et al. | 210/651 |

OTHER PUBLICATIONS

Guyton, A. C., *Textbook of Medical Physiology*, Chapter 72, 1986.
Thatcher, R. M., *J of Gerontol. Nurs.*, 98.6 Degrees F: What is Normal? 9 (1), pp. 22-27, Jan. 1983.
Acker, D. B., *Am. J. Obstet. Gynecol.*, The Normal Patients' Admission Temperature 157 (2), pp. 308-311, Aug. 1987.
Wailoo, M. P., *Arch. Dis. Child*, "Sleeping Body Temperatures . . . " 64 (4) pp. 596-599, 4/1989.
Davis, C., *J Gerontol. Nurse.*, "Circadian Rhythms: Charting Oral . . . ", 15 (4), pp. 34-39, Apr. 1989.

*Primary Examiner*—W. Gary Jones
*Attorney, Agent, or Firm*—Fay, Sharpe, Beall, Fagan, Minnich & McKee

[57] ABSTRACT

A method for more selectively removing macromolecules from a plasma solution, whereby plasma containing the macromolecules to be removed is provided and heated to a temperature near or above normal body temperature but below the boiling point of the plasma solution. The heated plasma solution is filtered while at a temperature near or above normal body temperature but below its boiling point with a membrane filter to remove selectively macromolecules from the plasma solution. An apparatus for accomplishing the foregoing is also provided.

20 Claims, 5 Drawing Sheets

THERMOFILTRATION OF PLASMA

This is a continuation of copending application Ser. No. 07/220,919 filed on 7-18-88 now U.S. Pat. No. 4,966,709, which is a continuation of Ser. No. 06/810,926, filed on Dec. 19, 1985, now abandoned.

BACKGROUND OF THE INVENTION

The present invention relates to the filtration of macromolecules from fluids, and more particularly to the removal of undesirable macromolecules from plasma solutions, by the process termed thermofiltration.

The separation of undesirable solutes from blood plasma through plasma filtration is a known method of treating diseases, wherein such diseases have in common undesirable elevated levels of plasma solutes, such as toxins, excessive antibodies, and other metabolic factors. Successful treatment of such diseases involves the removal of the undesirable plasma solutes from the blood plasma by membrane filtration.

Various methods of plasma filtration, including cascade filtration, double filtration, and cryofiltration have been developed. However, these methods contain a number of undesirable characteristics which limit their usage.

Applicants have noted a number of parameters associated with performance, including module design, membrane properties, plasma composition, and plasma and filtration temperature. Characteristics of the module which affect flow dynamics and in turn performance include, area, fluid and film dimensions, as well as properties of the separating membrane, including polymer type and microstructural features such as pore size, pore tortuosity, pore length, and pore number.

Variations in the plasma's composition also affects its filtration. Plasma from patients with different disease states or with differing macromolecule contents have different filtration characteristics. Manipulation of the plasma to effect changes in pH or electrolyte composition and the addition of anticoagulants such as heparin or other macromolecule-aggregating additives such as polyethylene glycol will effect filtration performance. Generally such manipulations are carried out for the purpose of augmenting the separation, by macromolecule aggregation or precipitation, of one or a group of solutes from the plasma.

Because of the number of parameters affecting filtration performance, temperature selection and its control has been demonstrated to be a key parameter in fluid separation. In order to augment the selective removal in a particular macromolecular range, it is extremely important to operate within the proper temperature range. In this respect, significant differences have been noted for comparable conditions of filtration (similar operating flows, modular types and plasma types) between cascade and double filtration, which operate at near ambient temperatures, and cryofiltration, which operates at temperatures below a set physiologic temperature.

Temperature control offers many advantages over the other parameters in that temperature control is the easiest controlled physical parameter, and that temperature control may be combined with the use of various complexing agents to increase the sensitivity of macromolecule removal. A specific example of this can be shown in the case of cryofiltration, where the addition of heparin aids in the formation of cryogel by forming complexes with fibronectin and fibrinogen at temperatures below 25° C.

Filtration at sub-physiologic temperature is effective for the removal of plasma constituents similar in size but differing in temperature sensitivity. A number of auto-immune diseases can be treated in this fashion, as has been described in the literature. The effectiveness of the treatment is attributed to the formation and removal of cryogel, which is composed of high concentrations of the macromolecules associated with autoimmune disease states. Thus, the separation in cryofiltration is not based on molecular size at physiologic temperature but on molecular size at reduced temperatures.

However, operation at a reduced temperature can, in fact, reduce the selectivity of molecule separation when size differences are great since aggregation or complex formation of small molecules may also occur at reduced temperatures. Therefore, for separation based on size differences at physiologic temperatures, it may be more advantageous to avoid cryogel formation.

Accordingly, it is an object of the present invention to provide an improved means of removing undesirable macromolecules from fluids in an effective and efficient manner.

SUMMARY OF THE INVENTION

In one aspect, the present invention relates to a method of selectively removing macromolecules from a plasma solution including the steps of providing a plasma solution containing the macromolecules to be removed, heating and/or maintaining the plasma at a temperature near or above normal body temperature but below the boiling point of the plasma solution, and filtering the warmed plasma solution while at a temperature near or above normal body temperature but below the boiling point with a membrane filter to remove more selectively macromolecules from the plasma solution. In addition, by heating the plasma solution, various macromolecules present within the plasma solution may become inactivated or denatured, aiding in their selective removal through plasma filtration.

In another aspect, the present invention concerns a method of selectively removing macromolecules from a plasma solution including the steps of securing a blood flow from a specimen, separating the blood flow into a concentrated cellular element stream and a plasma stream containing the macromolecules to be removed, heating or maintaining the plasma stream containing macromolecules to be removed to a temperature near or above normal body temperature but below its boiling point, filtering the warmed plasma stream while at a temperature near or above normal body temperature but below its boiling point with a membrane filter to remove more selectively macromolecules from the plasma solution to form a filtered plasma stream, combining the filtered plasma stream and said cellular element stream to form a processed plasma stream, and cooling and/or returning the processed stream plasma to the specimen.

In still another aspect, the present invention concerns a method of controlling conditions of lipoprotein abnormalities in a living organism by selectively removing macromolecules from a plasma solution including the step of securing a blood flow from a living organism, separating the blood flow into a concentrated cellular element stream and a plasma stream containing the macromolecules to be removed, heating or maintaining the plasma stream containing macromolecules to be removed to a temperature near or above normal body temperature but below its boiling point, filtering the heated plasma stream while at a temperature near or above normal body temperature but below its boiling point with a membrane filter to remove more selectively macromolecules from the plasma solution to form a filtered plasma stream, combining the filtered plasma stream and said cellular element stream to form a processed plasma stream, and cooling and/or returning the processed plasma stream to the living organism.

In still another aspect, the present invention concerns an apparatus for removing more selectively macromolecules from a plasma solution comprising a means of receiving and dividing a plasma containing solution containing macromolecules procured from a specimen into a concentrated cellular element stream and a plasma stream, a means of receiving, heating and/or maintaining the plasma stream to a temperature near or above normal body temperature but below its boiling point, a means of receiving and filtering the heated plasma stream to remove selective macromolecules, a means for receiving the filtered plasma stream from the filter means and for receiving the concentrated cellular element stream and combining the streams to form a processed stream substantially free of the macromolecules intended to be remove and a means of receiving and/or cooling the combination stream to normal body temperature for returning said fluid to the specimen.

In a further aspect, the present invention relates to a method of selectively removing macromolecules from a plasma solution including the steps of providing a plasma solution containing the macromolecules to be removed, heating the plasma to a temperature from about 35° C. to 60° C., and filtering the heated plasma solution to selectively remove macromolecules from the plasma solution.

In an additional aspect, the present invention relates to a method of selectively removing macromolecules from a plasma solution including the steps of providing a plasma solution containing the macromolecules to be removed, heating the plasma to a temperature from about 37° C. to 52° C., and filtering the heated plasma solution to selectively remove macromolecules from the plasma solution.

BRIEF DESCRIPTION OF THE DRAWINGS

The following is a brief description of the drawings which are presented for the purpose of illustrating the invention and not for the purpose of limiting same.

DETAILED DESCRIPTION OF THE INVENTION

Figure 1:
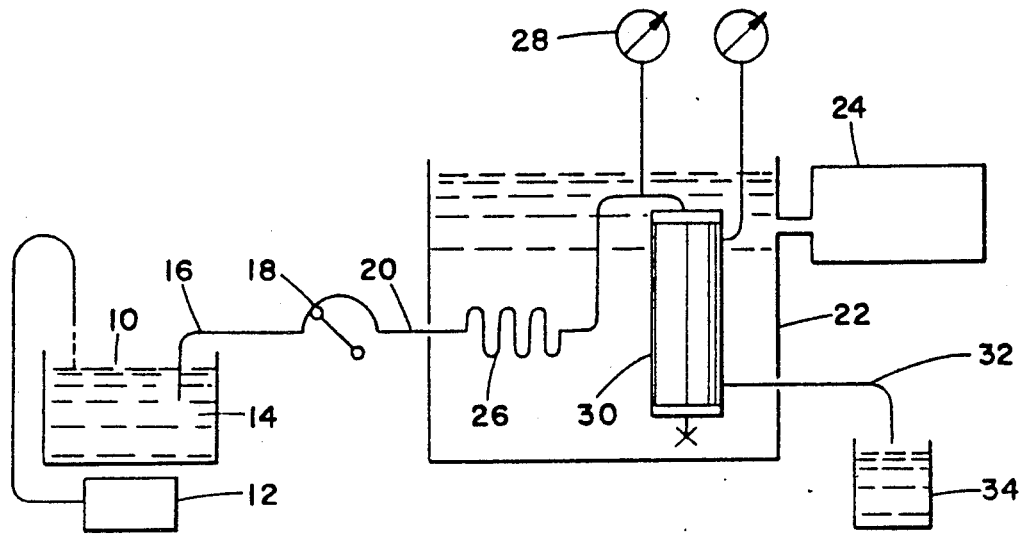
FIG. 1 shows the circuit used in in vitro filtration.

Applicant has discovered that thermofiltration offers many advantages over the conventionally known methods of plasma filtration. Thermofiltration is the removal of macromolecules from plasma by warming the plasma to a selective temperature near or above the normal physiologic temperature but not above its boiling point and filtering the warmed plasma with a membrane filter having a porosity that will remove the desired macromolecules. The critical advantages demonstrated by thermofiltration include the ability to filter a much greater volume of plasma at higher temperatures because plasma exposed to the higher temperature has less of a tendency to form deposits of undesirable solutes on the membrane media and the more selective removal of macromolecules based upon differences in sieving coefficients at higher temperatures.

Evaluations of multiple membrane filters for plasma filtration based on filter material, pore size, and structure indicate that the Kuraray Eval 4A module (ethylene and vinyl alcohol copolymer, Kuraray Co., Japan) and other modules of similar properties are particularly well suited for plasma solute fractionation by thermofiltration. Other suitable filters include those which utilize filter media consisting of polysulfone, polypropylene, nylon, polyester, cellulose acetate, collagen and the like.

Applicants have demonstrated that sieving coefficients of some macromolecules are significantly higher at 37° C. and 42° C. than at 25° C. for the Kuraray Eval 4A module. (Table I below). Particularly noteworthy are the higher sieving of HDL cholesterol, IgG, fibringen, total protein, and albumin at 37° to 42° C. In addition, as a result of the reduction of cryogel formation at these higher temperatures, a much greater volume of plasma can be filtered. This is because at near or above normal physiologic temperatures solute aggregation is kept to a minimum, and separation is due to the molecular size differences of the solutes and not the aggregate compositions.

TABLE I

| Sieving coefficients for various macromolecules. | | | | | | | |
|---|---|---|---|---|---|---|---|
| | TP | Alb | Glb | Fib | IgG | IgA | IgM | Volume Processed (ml) |
| 25° C. | 0.61 | 0.71 | 0.48 | <0.06 | 0.36 | 0.21 | 0.15 | 1,000 |
| 37° C. | 0.74 | 0.82 | 0.59 | 0.13 | 0.55 | 0.51 | 0.17 | 1,000~3,000 |
| 42° C. | 0.74 | 0.86 | 0.59 | 0.26 | 0.57 | 0.46 | 0.18 | 1,000~3,000 |

| | T Chol | LDL | HDL | TG | Volume Processed (ml) |
|---|---|---|---|---|---|
| 25° C. | 0.07 | 0.03 | 0.71 | 0.13 | <1,000 |
| 37° C. | 0.06 | 0.02 | 0.84 | 0.11 | 1,000~3,000 |
| 42° C. | 0.04 | 0.03 | 0.97 | 0.13 | 1,000~3,000 |

All macromolecules are from the same plasma source. Heparin dosage: 1,000 U/L.
TP: total protein; Alb: albumin; Glb: globulin; Fib: fibrinogen; T Chol: total cholesterol; LDL: low density lipoprotein; HDL: high density lipoprotein; TG: triglycerides.

Moreover, thermofiltration is an effective method of removing pyroglobulins from plasma solutions. Pyroglobulins are serum globulins that precipitate or gel upon heating. Normally, pyroglobulins are not found in serum of normal individuals. Rather they are readily associated with macroglobulinemia and other lymphoproliferative or multiple myeloma disorders. Heating a serum containing pyroglobulins to 55°-56° C. results in gel formation, which can be effectively removed from the serum through plasma filtration. Similarly, proteins and other immunoglobulins which effectively denature or coagulate upon heating may also be selectively removed through thermofiltration.

As a consequence of the above advantages of thermofiltration over conventionally known methods of plasma separation, thermofiltration can be used to selectively remove pathologic macromolecules from blood in on-line and off-line plasma treatments, while at the same time allowing for the passage or return of beneficial plasma proteins. The advantage of this type of treatment can be clearly shown in the therapeutic control of cholesterol.

Cholesterol has been determined to be an important component of arterial plague formation in artherosclerosis as well as in hypercholosterolemia. Cholesterol circulates in the blood linked to large protein molecules. One form of cholesterol carrying protein, called low-density lipoprotein (LDL), is known to promote atherosclerosis. About two-thirds or more of total blood cholesterol is transported in LDL. Another form, called high-density lipoprotein (HDL), is known to be protective against the disease process. Therefore, the selective removal of LDL and maintenance of HDL is important in the treatment of atherosclerosis and the therapeutic control of hypercholesterolemia.

Recently, plasma exchange has been utilized for the removal of plasma and its replacement with electrolyte solutions and/or plasma products in familial hypercholesterolemia patients. However, these methods are nonselective and remove proportionately low density lipoproteins (LDL) with high-density lipoproteins (HDL) and other plasma proteins which are beneficial to the patient. In addition, several methods have been studied for the selective removal of LDL, including anti-LDL-antibody Sepharose columns, and combinations of heparin precipitation and bicarbonate dialysis, however, membrane filtration offers many advantages over these methods in terms of biocompatibility and treatment cost effectiveness.

The selective removal of LDL cholesterol from plasma by thermofiltration can be demonstrated under both in vitro and ex vivo conditions. In vitro pertains to conditions of experimentation in a laboratory setting, whereas ex vivo pertains to conditions of extracorporeal circulation with living organisms.

I. In Vitro Filtration

Various types of plasma are used in vitro to evaluate the temperature effect on selective cholesterol removal. The in vitro filtration tests are carried out with the various types of plasma at varying temperatures according to the extracorporeal circuit demonstrated in FIG. 1.

In FIG. 1, one unit per ml. heparin (heparin sodium injection, Invenex Lab., OH) is added to plasma pool 10 wherein the plasma is kept at approximately 37° C. by heat controller 12 and magnetic stirrer 14. Plasma is drawn from plasma pool 10 into line 16 and fed into plasma pump 18 of a plasma flow rate of 15 ml/min. The plasma is pumped from plasma pump 18 into line 20 and then into water bath 22 which is controlled by thermoregulater 24. Within water bath 22, the plasma passes through heat exchanger 26 and passes by pressure gauge 28 into filter 30, where the LDL cholesterol is retained and the HDL cholesterol and albumin substantially pass through. From filter 30, the filtered plasma minus LDL cholesterol flows through line 32 into filtrate collection pan 34.

The following specific examples further illustrates the practice of the present invention.

EXAMPLE I

Familial type II hypercholesterolemic plasma (FHC) was procured by repeated centrifugal plasma exchange. The in vitro filtration tests were carried out with the FHC plasma and the Kuraray EVAL 4A membrane filter at temperatures of 4°, 25°, 37°, 42° and 47° C., respectively, according to the extracorporeal circuit demonstrated in FIG. 1 and as described above. The mean sieving coefficients (sc), the plasma volume processed, and the total amount of LDL and HDL cholesterol were determined at the above temperatures by the following calculations.

$$\text{sieving coefficient } (sc) = \frac{\text{Concentration in Filtrate (mg/dl)}}{\text{Concentration in filter inlet (mg/dl)}}$$

wherein a sieving coefficient of 0.9 to 1 indicates little or no separation or removal of the macromolecule from plasma, and a sieving coefficient of 0 to 0.1 indicates substantially total removal of macromolecules from plasma.

Removal Amount (g) = Concentration in plasma pool
(g/dl) X(1 − sc) × Processed Volume (dl)

RESULTS

Table II outlines the volume processed and the mean sieving coefficients for total cholesterol, HDL cholesterol, LDL cholesterol, and albumin at varying temperatures. The results indicated that greater than 85% of the total cholesterol and 90% of LDL cholesterol were removed while over 70% of albumin and 60% of HDL cholesterol were passed through the filter. The sieving coefficients of HDL cholesterol and albumin increased with increasing temperature while LDL cholesterol was independent of temperature.

TABLE II

| Mean sieving coefficients and plasma volumes processed at varying temperatures; in vitro filtration test of Kuraray Eval 4A (1.0M surface area) using familial hypercholesterolemic plasma. | | | | |
|---|---|---|---|---|
| Temp (°C.) | Processed Volume (ml) | Mean Sieving Coefficients | | |
| | | Total Chol | HDL Chol | LDL Chol | Alb |
| 4 | 365 | 0.10 | 0.58 | 0.07 | 0.72 |
| 25 | 1135 | 0.11 | 0.76 | 0.10 | 0.84 |
| 37 | 1780 | 0.12 | 0.67 | 0.06 | 0.81 |
| 42 | 2150 | 0.16 | 0.72 | 0.08 | 0.91 |
| 47 | 2350 | 0.14 | 0.79 | 0.08 | 0.94 |

Figure 3:
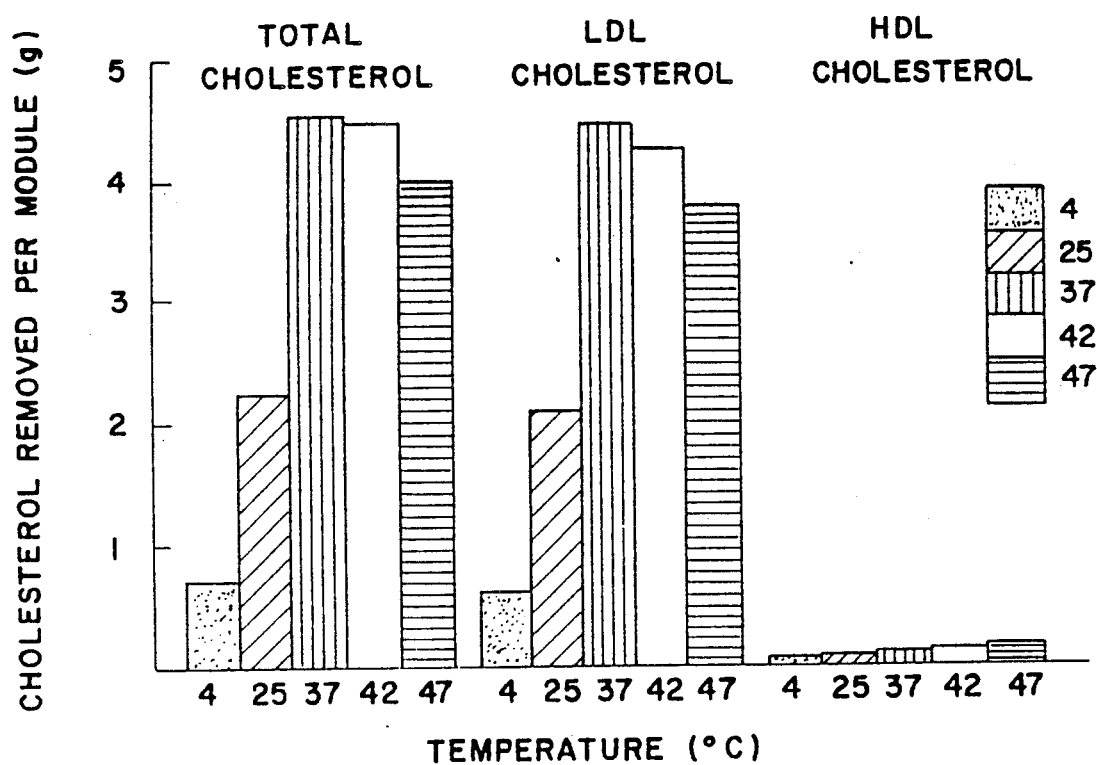
FIG. 3 shows the amount of cholesterol removed at varying temperatures for in vitro filtration.

FIG. 3 demonstrates that cholesterol removal differs at varying temperatures. At 37° to 42° C., the removed LDL cholesterol amount is largest (4.5 g module), while HDL cholesterol is below 0.1 g. Removal amount per module was limited by the maximum $P_{tm}$ (300 mm Hg) permitted.

Conclusion

Thermofiltration is highly effective in selectively removing large quantities of LDL cholesterol from plasma while retaining large quantities of useful HDL cholesterol and albumin under in vitro conditions. The in vitro membrane filtration of FHC plasma with the EVAL 4A filter permits near complete rejection of LDL cholesterol with high sieving or retainment of HDL cholesterol and albumin. The sieving coefficients of HDL cholesterol and albumin increased with increasing temperature, while the sieving coefficient of LDL cholesterol was near complete rejection at all temperatures. Thus, membrane filtration near or above physiologic temperatures, i.e., thermofiltration, improves the selectivity of LDL cholesterol removal over that of HDL cholesterol and albumin.

Moreover, thermofiltration also permits higher plasma volumes to be processed. This is a result of the reduction of cryogel formation and less removal of solutes not intended to be removed at the elevated temperatures. Also, higher volumes of plasma are processed and larger quantities of cholesterol are removed per unit module.

EXAMPLE II

In vitro module filtration tests were carried out with normal human plasma (NHP) and sclerosing cholangitis plasma (SCP) using the Eval 4A (copolymer of ethylene and vinyl alcohol; surface area 2.0 m$^2$) at 4°, 25°, 37°, 42°, 47° and 52° C., respectively, according to the extracorporeal circuit demonstrated in FIG. 1 and as described above. The NHP was procured by filtration at 37° C. of outdated citrated plasma using the Toray PS-05 plasma separator (polymethylmethacrylate; surface area 0.5 m$^2$; Toray Industries, Japan). The SCP was procured by membrane plasma exchange. The SCP differed from the NHP in that the SCP had 1.5 fold higher fibrinogen and four fold higher LDL cholesterol concentrations with similar levels of albumin and antithrombin III when compared to NHP.

All filtration tests were carried out with a plasma flow of 30 ml/min. Changes in inlet pressure were monitored as a function of the transmembrane pressure and reflect membrane plugging.

Samples obtained pre and post filtration were analyzed for various biochemical solutes including albumin (Alb), fibrinogen (Fib), total cholesterol (T Chol), LDL cholesterol (LDL Chol), HDL Cholesterol (HDL Chol), antithrombin III (AT III) and heparin. Alb was measured with an autoanalyzer (SMA-II, Technicon Instrument Co., Tarrytown, NY) by the bromocresol green method. Fib was measured by the Fibrosystem (BBL, Ockeysville, MD). T chol and triglycerides were measured with an autoanalyzer (AA II, Technicon Inst. Co.) using the cholesterol oxidase-peroxidase enzymatic method. LDL chol was calculated as: T chol-HDL chol-1/5 triglycerides. HDL chol was measured by the dextran-sulfate-Mg$^{2+}$ precipitation method. Antithrombin III and heparin were measured by the Protopath antithrombin III and heparin synthetic substrate assay (American Dade, Miami, FL).

RESULTS

Figure 4A:
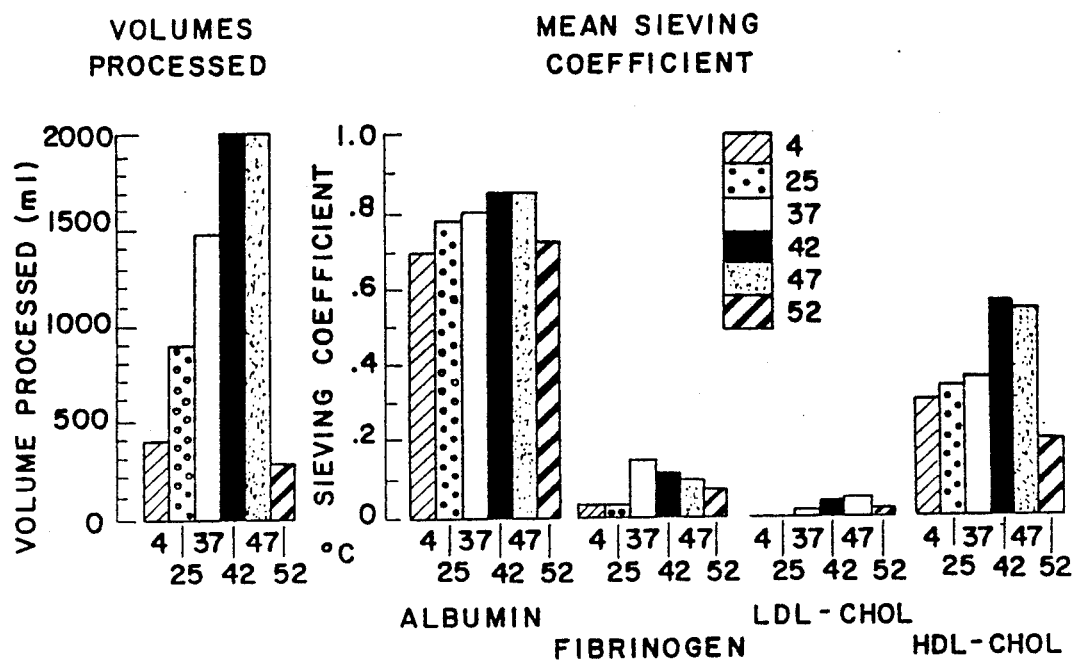
FIGS. 4A and B show the mean sieving coefficients with various kinds of plasma. (Kuraray Eval 4A module; In vitro at 37° C.)
Figure 4B:
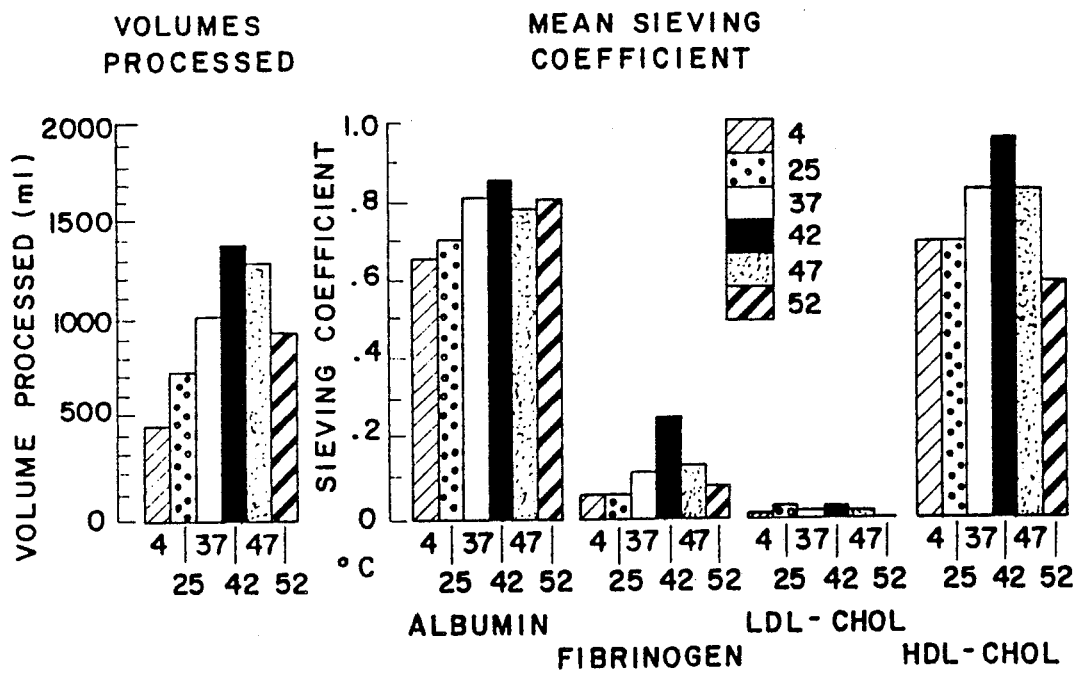

FIGS. 4A and 4B show the volumes processed and the sieving coefficients for the filtration of NHP and SCP over the temperature range of 4° to 52° C. In both plasmas higher volumes were processed as the temperature was increased from 4° to 52° C. However, the volume processed did not increase at temperatures over 42° C. and dropped significantly at 52° C. Sievings for Alb increased with increasing temperature from 4° to 42° C. and thereafter also dropped. A similar tendency can be seen in fibrinogen. Significant increases of HDL chol sieving were observed in the temperature range of 4° to 42° C. where no major changes in LDL chol were noted. HDL chol sieving also dropped at 52° C. Total removal of LDL chol and removal ratios of HDL chol and Alb to LDL chol were listed in Table III. Maximum removal amounts of LDL chol and minimal removal of HDL chol and Alb versus LDL chol removal were obtained at 42° C.

TABLE III

Total removal and ratios of HDL/LDL and albumin/LDL cholesterol removal using NHP and SCP patients plasma at varying temperatures.

| Plasma | | Temp °C. | | | | | |
|---|---|---|---|---|---|---|---|
| | | 4° | 25° | 37° | 42° | 47° | 52° |
| NHP | LDL Chol (mg) | 130 | 347 | 932 | 1854 | 1549 | 198 |
| | HDL chol / LDL chol | 0.95 | 0.76 | 0.45 | 0.19 | 0.23 | 0.48 |
| | Alb / LDL chol | 31.1 | 18.2 | 10.5 | 5.6 | 6.5 | 14.1 |
| SCP | LDL chol (mg) | 887 | 1458 | 2368 | 3130 | 2790 | 1216 |
| | HDL chol / LDL chol | 0.016 | 0.021 | 0.008 | 0.001 | 0.007 | 0.05 |
| | Alb / LDL chol | 6.2 | 5.6 | 2.9 | 2.2 | 3.2 | 4.8 |

NHP = normal human plasma
SCP = sclerosing cholangitis plasma

Conclusion

These results suggest that operation at near physiologic temperature is promising for prevention of heparin induced aggregation which occurs below physiologic temperature and filter plugging caused by these deposits when smaller pore size membranes are used to separate molecules. As shown in FIGS. 4A and 4B, filtration above physiologic temperature (up to 47° C.) produces higher volumes processed and a higher passage of albumin and HDL chol. These results indicate that plasma filtration near or above 37° C., thermofiltration, is promising for clinical use in the separation of plasma solutes based on size differences (i.e., LDL selective separation vs. HDL sieving).

II. Ex Vivo Filtration

Ex vivo filtration is the continuous on-line filtering of plasma with living organisms. The ex vivo filtration tests were carried out at 37° C. according to the extracorporeal circuit demonstrated in FIG. 2.

Figure 2:
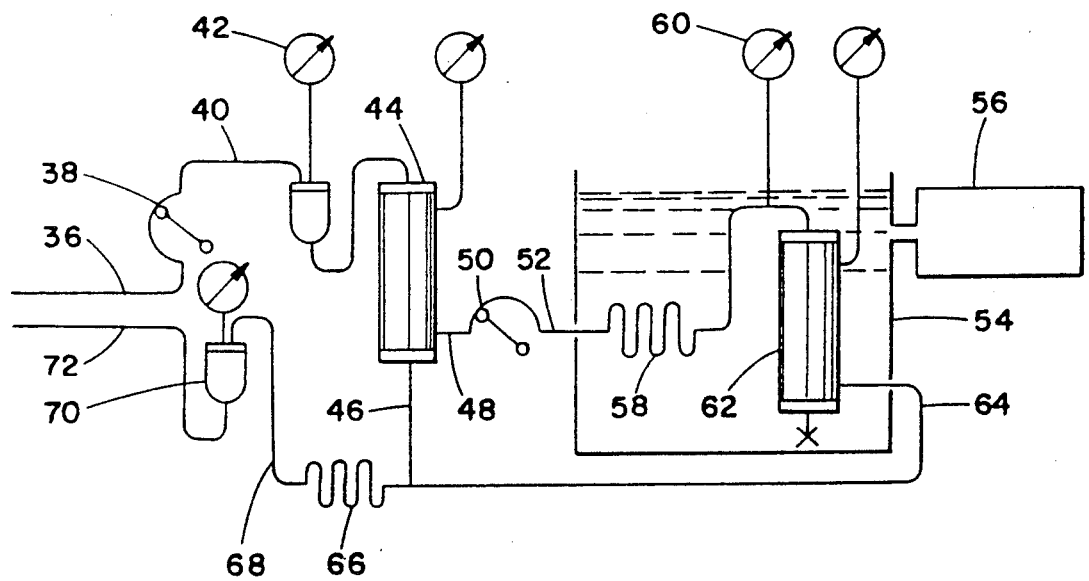
FIG. 2 shows the extracorporeal circuit used in ex vivo or clinical filtration.

Referring to FIG. 2, blood is drawn from the artery of a living organism into line 36 and fed into a pump 38 from which it is pumped into a line 40, passing by pressure gauge 42 and into plasma separator 44, where the plasma and blood cellular elements are separated. The concentrated blood cellular elements are fed into line 46, while the plasma is fed into line 48. From line 48, the plasma flows through pump 50 to line 52 where it enters water bath 54 controlled by thermo-regulator 56.

Within water bath 54, the plasma passes through heat exchanger 58 and by pressure gauge 60 into filter 62, where the LDL cholesterol is substantially retained and the HDL cholesterol, albumin, and other low molecular weight macromolecules substantially pass through.

From filter 62, the filtered plasma which is essentially deficient in LDL cholesterol flows through line 64 and is intermixed with the blood cellular elements of line 46. The mixture then is either cooled to body temperature in heat exchanger 66, or passed into line 68 where it passes pressure gauge 70 and is fed into line 72 and returned to the vein of a living organism in a continuous process.

The following specific examples further illustrate the practice of the present invention.

EXAMPLE 3

As a result of the similarity of lipoproteins and its suitable body size for on-line filtration, a hypercholestrol dog was the model chosen for ex vivo filtration. The thyroidectomized/diet canine model is well established and has been studied extensively. Using this model, three different cholesterol level ranges up to 600 mg/dl (normal, 120 mg/dl) were evaluated.

Arterio-venous (AV) fistulae were constructed in two healthy male mongrel dogs weighing from 24 to 30 kg. As a control, dogs were maintained with a normal diet (lab Canine Diet 5006; Lab Chow, St. Louis, MO). As a middle cholesterol concentration model, the same dog was maintained with the same diet after surgical thyroidectomy. As a high cholesterol concentration model, the dog was maintained with a special diet that consisted of the normal meal with 4% hydrogenated coconut oil and 0.75% cholic acid added (TD 75337, Taklad, Madison, WI) after thyroidectomy.

Ex vivo filtration tests were carried out in the dogs at different cholesterol levels under general anesthesia with nitrous oxide gas and nembutal injection (Nembutal sodium solution, Abbott Lab, IL). An AV fistula was used for blood access and 200 unit/kg heparin was injected as an anticoagulant. Plasma was separated in the on-line extracorporeal system using a membrane plasma separator (Mitsubishi 60TW, polyethelene, Mitsubishi Rayon Co., Japan). The separated plasma was filtered using the same method as in vitro filtration (at 37° C.) and the filtered plasma was then recombined and returned to the dog (FIG. 3). Blood and plasma flows employed were 60 and 15 ml/min, respectively. One calculated plasma volume was filtered. Eight hundred to 1000 ml of lactated Ringer's solution was infused intravenously during the extracorporeal circulation.

Samples were drawn simultaneously from the arterial and plasma lines of the filter inlet and outlet when one half and one volume were processed, and pre- and post-treatment. At one hour and 1, 3, 7, 14 and 21 days post treatment, blood samples were taken following 14 to 16 hours fasting. Dogs were fed the same diet as before filtration ad libitum. Biochemical measurements included cholesterol and triglyceride (automatic analysis AA II, Technicon Instrument Co., NY), HDL cholesterol (Dextran Sulfate MgCl$_2$ precipitation procedure), in addition to routine serum multiple analysis (SMA-II system, Technicon Instrument Co.) and hematological analysis (automated cell counter, Coulter Electronics Inc., FL).

The LDL cholesterol concentration of human plasma was calculated using the equation: total cholesterol−HDL cholesterol−1/5 triglyceride. The LDL-VLDL cholesterol concentration in dogs was calculated as follows: total cholesterol HDL cholesterol. The lipoprotein fractions were prepared for analysis by preparative ultracentrifuge (human LDL; $1.006 < d < 1.063$, human HDL; $1.063 < d < 1.21$, canine LDL-VLDL; $d < 1.063$, canine HDL; $1.087 < d < 1.21$), where d = density. Lipoprotein particle sizes were measured using negative straining electron micrographs. These fractions of canine lipoproteins are not homogeneous but are comparable to the fractions obtained by precipitation methods.

RESULT

Table IV outlines cholesterol concentrations at the various stages of the dog model. Total cholesterol, particularly LDL-VLDL cholesterol, was increased and the ration of LDL-VLDL cholesterol to HDL cholesterol was increased over 10 times. Albumin showed no significant change. On-line plasma filtration was carried out at each cholesterol level. Transmembrane pressure ($P_{tm}$) of the plasma separator was stable throughout the procedure. Sieving coefficients of albumin and total cholesterol and other macromolecules were over 95%. The $P_{tm}$ of the macromolecule filter increased gradually during the perfusion. The $P_{tm}$ values at one plasma volume processed ranged from 10 to 256 mmHg. Significant differences in $P_{tm}$ changes were not dependent on cholesterol concentrations.

TABLE IV

Cholesterol and albumin levels on canine hypercholesterolemic model.

| | CHOLESTEROL LEVEL (mg/dl) | | | Albumin level |
|---|---|---|---|---|
| | TOTAL | HDL | LDL-VLDL | (g/dl) |
| I; | 137 ± 24 | 115 ± 15 | 21 ± 9 | 3.00 ± 0.06 (n = 3) |
| II; | 395 ± 30 | 181 ± 13 | 214 ± 17 | 3.25 ± 0.07 (n = 2) |
| III; | 600 ± 14 | 219 ± 30 | 382 ± 16 | 3.25 ± 0.21 (n = 2) |

I: Normal dog with normal diet
II: Thyroidectomized dog with normal diet
III: Thyroidectomized dog with 4% hydrogenated coconut oil and 0.75% cholic acid addition on normal diet Table V outlines mean sieving coefficients at the varying cholesterol level. LDL-VLDL cholesterol was highly rejected by the plasma filter, whereas albumin and HDL cholesterol showed high sieving. The sc of the LDL-VLDL cholesterol decreased with increasing cholesterol.

TABLE V

Mean sieving coefficients of macromolecule filter; ex vivo on-line filtration test (37° C.) of Kuraray Eval 4A on different cholesterol levels.

| | CHOLESTEROL | | | |
|---|---|---|---|---|
| | TOTAL | HDL | LDL-VLDL | ALBUMIN |
| I; | 0.60 ± 0.10 | 0.63 ± 0.09 | 0.39 ± 0.07 | 0.88 ± 0.07 (n = 3) |
| II; | 0.42 ± 0.08 | 0.61 ± 0.11 | 0.32 ± 0.01 | 0.95 ± 0.06 (n = 2) |
| III; | 0.34 ± 0.05 | 0.59 ± 0.09 | 0.19 ± 0.04 | 0.93 ± 0.04 (n = 2) |

Mean ± Standard Deviation

Figure 5:
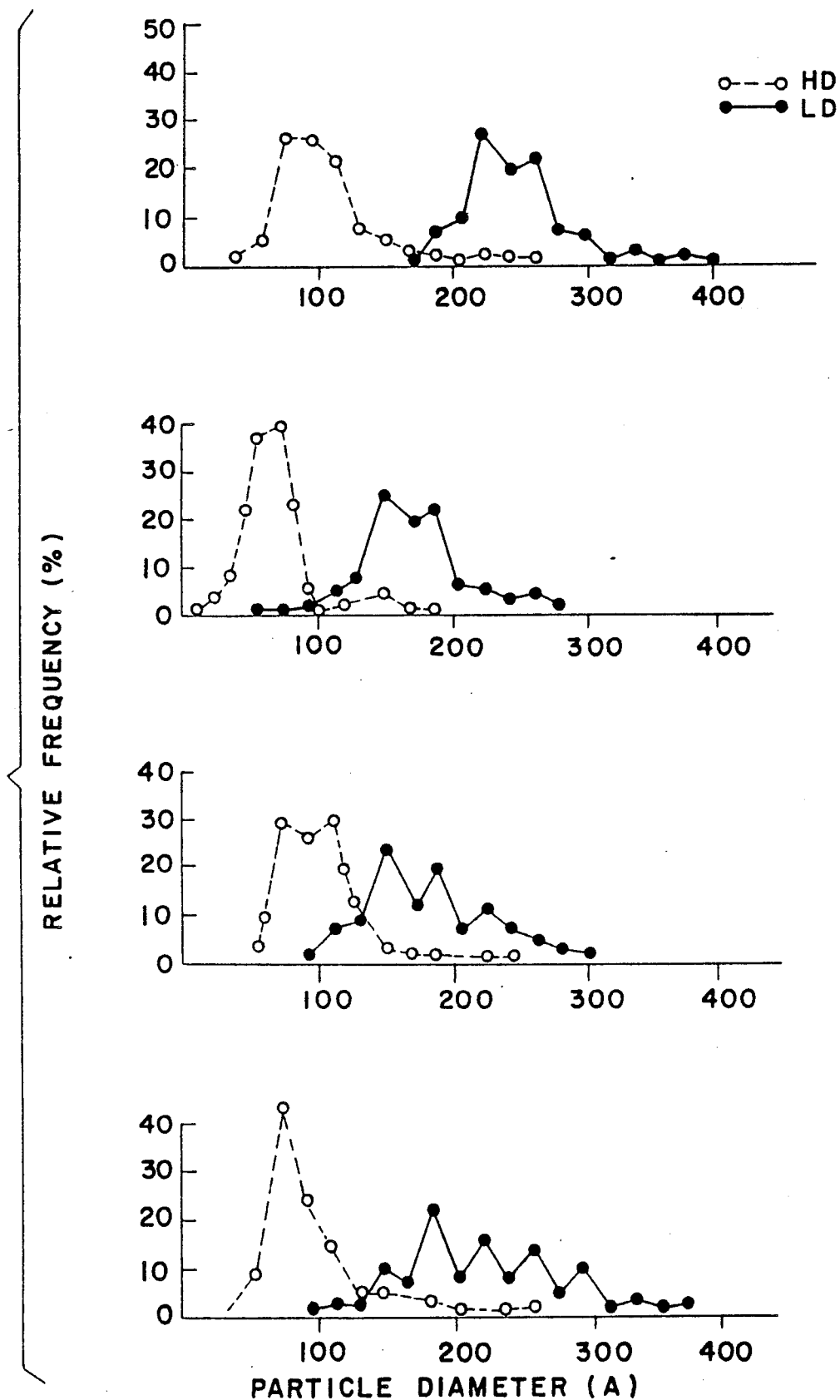
FIG. 5 shows the particle size distribution of the lipoprotein for the FHC plasma and the dog plasma with various cholesterol levels.

FIG. 5 shows the particle size distribution of the lipoprotein for the FHC plasma and the dog plasmas with various cholesterol levels. The size difference between the HDL and LDL of FHC plasma was greater than that of the dog plasmas. The particle diameters and deviation of LDL-VLDL in dog plasmas also increased, but not in as great degree as with the human plasma. The HDL size was not significantly different among the groups.

Figure 6:
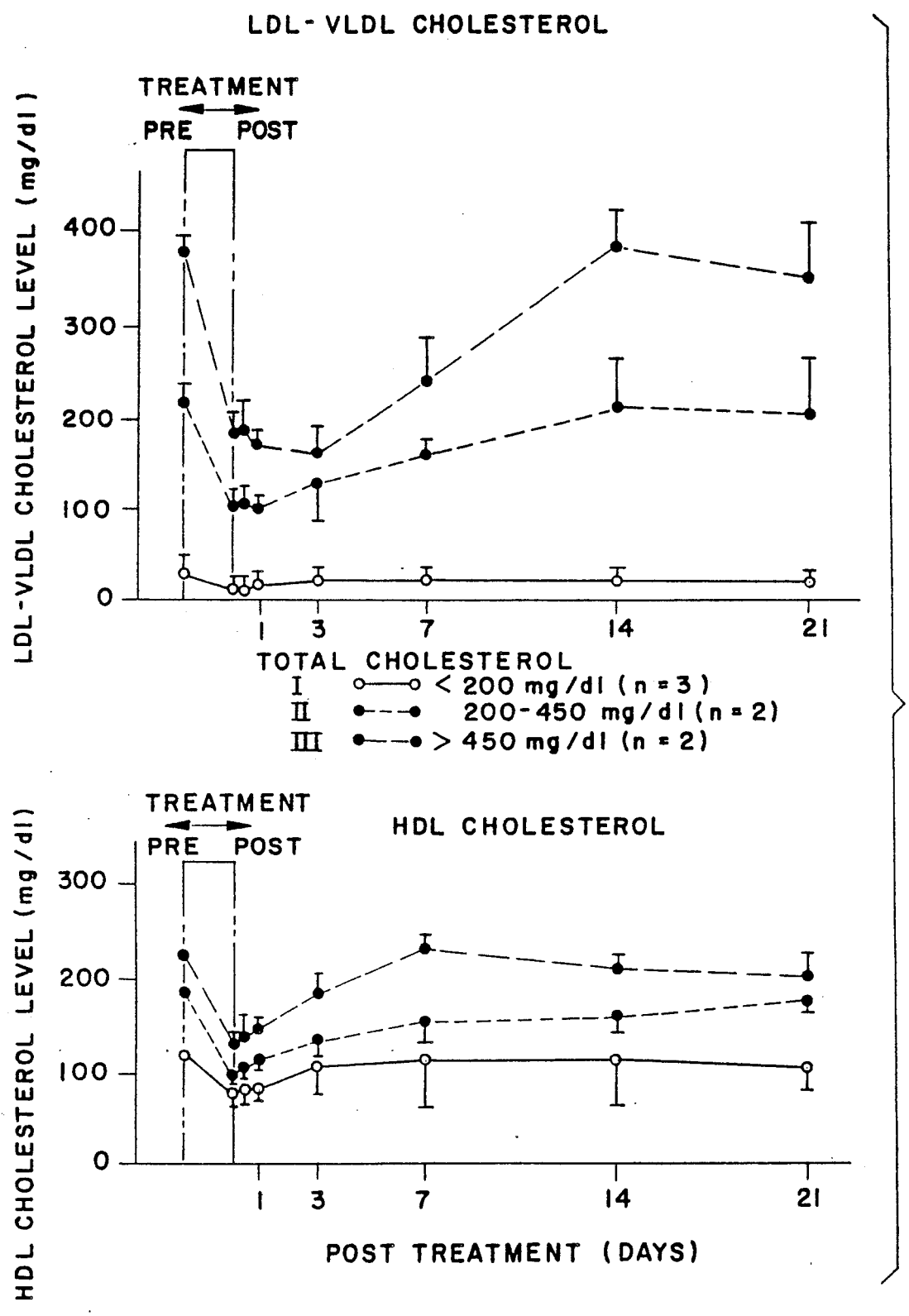
FIG. 6 shows the post treatment recovery in a dog of LDL-VLDL and HDL cholesterol.

FIG. 5 shows the post treatment recovery of HDL-VLDL and HDL cholesterols. Recovery of LDL-VLDL cholesterol was prolonged in the higher cholesterol level groups. For Groups II and III, it took about 2 weeks to return to pre-treatment values. HDL cholesterol recovery was constant and returned to pre-values within 7 days for all groups. FIG. 6 shows the changes in the LDL-VLDL cholesterol/HDL cholesterol ratios. The ratio decreased during the post filtration periods and was maintained at a lower level for 14 days. The tendency for a higher reduced ratio for longer periods in comparison to the pre or post treatment values was greater in Group III which had the highest cholesterol.

Conclusion

The data indicates that lipoprotein particle size and sieving coefficients are highly cholesterol concentration dependent. As the cholesterol concentration increases, lipoprotein particle size (particularly LDL-VLDL) increases, sieving decreases and the total cholesterol (LDL-VLDL cholesterol) removal increases.

A comparison of the sieving coefficients indicates that canine LDL-VLDL sieving is greater than that of human LDL. This correlation is explained by the particle size study which indicates larger deviations and overlaps between canine LDL-VLDL and HDL, making it more difficult to separate the lipoproteins in canines than in humans. These results indicate that thermofiltration would be quite effective in humans in regard to the selective removal of lipoproteins.

Moreover, the data indicates that there is a more prolonged recovery of the LDL-VLDL cholesterol in the more hypercholesterolemic stages, while HDL cholesterol recovery remains relatively normal. The reduction of LDL cholesterol with preservation of HDL cholesterol by thermofiltration and the prolonged recovery of LDL-VLDL cholesterol with the maintenance of lower LDL/HDL ratio is highly suggestive of an effective method of treating lipoprotein abnormalities.

EXAMPLE IV

Initial clinical thermofiltration procedures were performed on a secondary hypercholesterolemia patient. The patient selected for the trial was a 39 year old man who had a high concentration (210–450 mg/dl) of cholesterol and a very high LDL/HDL cholesterol ratio (8–30) due to the cholestasis of sclerosing cholangitis.

The thermofiltration tests were carried out according to the on-line system exhibited in FIG. 2. The blood flow was set at 100 ml/min and the plasma flow at 30 ml/min. The Toray PS-05 (Toray Industries, Tokyo, Japan), and Asahi Plasmaflo (AP 0511: Asahi Medical Co. Tokyo, Japan) modules were used as the plasma separator, and the EVAL 4A 2.0 m² (Kuraray Co. Osaka, Japan) was used as the plasma filter. The filter and a warmer plate were wrapped with an electric heating pad to maintain the temperature at 37° C. in the cryochamber of the Cryomax (Cryomax 360; Parker Biomedical, Irvine, CA, U.S.A.). For anticoagulation, 5000 U of heparin was injected as a bolus prior to initiation of the extracorporeal circulation. The processed plasma volume and transmembrane pressure were monitored continuously throughout the procedure. The filtration was carried out until the transmembrane pressure ($P_{tm}$) of the plasma filter reaches 500 mm Hg. Samples were drawn simultaneously from the plasma inlet and outlet lines of the filter when the $P_{tm}$ reached 150 and 300 mm Hg to calculate the sieving coefficients (sc). Solute sieving was calculated as concentration in the filtrate divided by the concentration in the plasma inlet to the plasma filter. Biochemical measurements included cholesterol and triglyceride (automatic analysis AAII, Technicon Instrument Co., Tarrytown, NY, U.S.A.), and HDL cholesterol (dextran sulfate $MgCl_2$ precipitation procedure), in addition to routine serum multiple analysis (SMA-II, Technicon Instrument Co.). The filter was removed from the circuit following plugging, and the plasmapheresis procedure was changed to plasma exchange, using 5% albumin solution as a substitution fluid. Plasma exchange was continued until one calculated plasma volume (2893 ml) was processed by plasma exchange alone.

In vitro filtration studies were done using the same filter, the same temperature, and plasma from the same patient as described in Example I.

RESULTS

The procedure was well tolerated by the patient and no adverse reactions were noted. No substitution fluid was used during the thermofiltration phase. To a $P_{tm}$ of 500 mm Hg. 1355±275 ml (1160 and 1540) ml of plasma were filtered and 1117±183 ml (980 and 1253 ml) were filtered to a $P_{tm}$ of 300 mm Hg. The course of $P_{tm}$ versus the filtered volume was comparable to in vitro studies with this patient's plasma, as was the filtered volume (1060 ml processed to 300 mm Hg of $P_{tm}$ in vitro).

There was near complete rejection for LDL+VLDL cholesterol (sc=0.02) and high passage of albumin (sc=0.75) and HDL cholesterol sc=0.78). Fibrinogen sieving was low (0.07). These results were comparable to the in vitro filtration results. (Table VI below).

TABLE VI

Concentration and sieving coefficients (sc) of solute (mean ± SD)

|  | Concentration | sc |
|---|---|---|
| Clinical (Ex Vivo)* | | |
| Total protein (g/dl) | 6.8 ± 1.0 | 0.64 ± 0.09 |
| Albumin (g/dl) | 3.2 ± 0.2 | 0.75 ± 0.06 |
| Total cholesterol (mg/dl) | 181 ± 47 | 0.09 ± 0.00 |
| HDL cholesterol (mg/dl) | 17 ± 7 | 0.78 ± 0.09 |
| LDL cholesterol (mg/dl) | 140 ± 40 | 0.01 |
| LDL-VLDL cholesterol (mg/dl) | 163 ± 41 | 0.02 ± 0.01 |
| Fibrinogen (mg/dl) | 286 ± 84 | 0.07 ± 0.03 |
| In vitro** | | |
| Total protein (g/dl) | 6.2 ± 0.3 | 0.72 ± 0.02 |
| Albumin (g/dl) | 3.6 ± 0.1 | 0.82 ± 0.03 |
| Total cholesterol (mg/dl) | 274 ± 2 | 0.06 ± 0.01 |
| HDL cholesterol (mg/dl) | 11 ± 3 | 0.84 ± 0.08 |
| LDL cholesterol (mg/dl) | 228 ± 12 | 0.02 ± 0.02 |
| LDL-VLDL cholesterol (mg/dl) | 263 ± 5 | 0.03 ± 0.02 |
| Fibrinogen (mg/dl) | 298 ± 28 | 0.13 ± 0.03 |

HDL: high density lipoproteins; LDL: low density lipoproteins; VLDL: very low density lipoproteins; $P_{tm}$: transmembrane pressure.
*Mean value of four samples, taken at $P_{tm}$ of 150 mm Hg and 300 mm Hg from each of two treatments.
**Mean value of three filtration tests at the same conditions.

CONCLUSION

Sieving coefficients of LDL cholesterol (0.02), HDL cholesterol (0.78) and albumin (0.75) demonstrate the selectivity of thermofiltration. These results are comparable to in vitro filtrations tests using the plasma of the same patient. The advantage of this system compared to plasma exchange is the maintenance of HDL (antiatherogenic lipoprotein) and other essential plasma solutes that would be discarded in plasma exchange. Thermofiltration is more selective than membrane schemes without temperature control and simpler to apply, as it does not require other plasma treatment steps or the addition of potentially harmful chemical additives. Moreover, abnormal concentrations of various proteins (such as immunoglobulins) can also be effectively removed by thermofiltration.

While there have been described herein what are at present considered to be the preferred embodiments of this invention, it will be apparent to those skilled in the art that various changes and modifications may be made therein without departing from the invention, and it is, therefore, intended in the appended claims to cover all such changes and modifications as fall within the true spirit and scope of the invention.

What we claim is:

1. A method for selectively removing the low-density lipoproteins from a plasma solution while maintaining the level of the high-density lipoproteins in the solution, comprising the steps of:
   a) providing a plasma solution containing low-density lipoproteins and high-density lipoproteins;
   b) heating said plasma solution to a temperature which provides for the selective separation of the low-density lipoproteins from the plasma solution while maintaining the level of the high-density lipoproteins in the plasma solution due to the differences in the sieving coefficients of the lipoproteins at the higher heated temperature; and,
   c) thermofiltering the heated plasma solution with a membrane filter to selectively remove the low-density lipoproteins from the plasma solution while maintaining the level of the high-density lipoproteins in the solution by the differences in sieving coefficients of said low-density and high-density lipoproteins at the heated temperature.

2. The method of claim 1, wherein said plasma solution is a human plasma solution.

3. The method of claim 1, wherein said plasma solution is a canine plasma solution.

4. A method for selectively removing the low-density lipoproteins from a plasma solution while maintaining the level of the high-density lipoproteins in the solution, comprising the steps of:
   a) securing a blood flow from a specimen;
   b) separating the blood flow into a concentrated cellular element stream and a plasma stream containing low-density and high-density lipoproteins;
   c) heating the plasma stream containing the low-density and high-density lipoproteins to a temperature which provides for the selective separation of the low-density lipoproteins from the plasma solution while maintaining the levels of the high-density lipoproteins due to the differences in the sieving coefficients of the lipoproteins at the higher heated temperature;
   d) thermofiltering the heated plasma stream with a membrane filter to selectively remove, by the differences in sieving coefficients of said low-density and high-density lipoproteins at the heated temperature, the low-density lipoproteins from the plasma solution while maintaining the level of the high-density lipoproteins; and,
   e) combining the filtered plasma solution containing the high-density lipoproteins and said cellular stream to form a processed plasma stream.

5. The method of claim 4, wherein said plasma solution is a human plasma solution.

6. The method of claim 4, wherein said plasma solution is a canine plasma solution.

7. The method of claim 4, wherein said process stream plasma is cooled before it is combined with said cellular element stream.

8. An apparatus for selectively removing the low-density lipoproteins from a plasma solution while maintaining the level of the high-density lipoproteins in the solution comprising:
   a) a means for dividing a plasma solution into a concentrated cellular element stream and a plasma stream containing low-density and high-density lipoproteins;
   b) a means for heating said plasma stream to a temperature which provides for the selective separation of the low-density lipoproteins from the plasma solution while maintaining the levels of the high-density lipoproteins due to differences of the sieving coefficients of the lipoproteins at the higher heated temperature;
   c) a means for thermofiltering the heated plasma solution with a membrane filter to selectively remove, by differences in sieving coefficients of said low-density and high-density lipoproteins at the heated temperature, the low density lipoproteins from the plasma solution while maintaining the level of the high-density lipoproteins in the solution; and,
   d) a means for combining the filtered plasma stream containing the high-density lipoproteins and the concentrated cellular element stream to form a processed stream substantially free of low-density lipoproteins.

9. A method of selectively removing undesirable macromolecules from a plasma solution by thermofiltration including the steps of:
   a) providing a plasma solution containing the macromolecules to be removed;
   b) heating said plasma solution to a temperature which provides for the selective separation of the undesirable macromolecules from the plasma solution while maintaining the levels of the desired macromolecules due to differences in the sieving coefficients of the macromolecules at the higher heated temperature; and,
   c) thermofiltering said heated plasma solution while at a temperature at or above 35° C. but below its boiling point with a membrane filter to selectively remove macromolecules from the plasma solution by differences in sieving coefficients of said macromolecules at higher temperatures.

10. The method of claim 9, wherein said plasma solution is a human plasma solution.

11. The method of claim 9, wherein said plasma solution is a canine plasma solution.

12. The method of claim 9, wherein said membrane filter has a porosity less than the size of the selective macromolecules to be removed from the plasma solution.

13. The method of claim 9, wherein said macromolecules are separated from said plasma solution based on differences in sieving coefficients at elevated temperatures.

14. The method of claim 9, wherein said macromolecules to be removed are selected from the group consisting of low density lipoproteins (LDL), pyroglobulins, high molecular weight proteins and mixtures thereof.

15. The method of claim 9, wherein said plasma includes normal, sclerosing cholangitis and type IIa hypercholesterolemia plasma.

16. A method of selectively removing undesirable macromolecules from a plasma solution including the steps of:
   a) securing a blood flow from a specimen;
   b) separating said blood flow into a concentrated cellular element stream and a plasma stream containing macromolecules to be removed;
   c) heating said plasma stream containing macromolecules to be removed to a temperature which provides for the selective separation of the undesirable macromolecules from the plasma solution while maintaining the levels of the desired macromolecules due to differences in the sieving coefficients of the macromolecules at the higher heated temperature;
   d) filtering said heated plasma stream while at a temperature at or above 35° C. but below its boiling point with a membrane filter to selectively remove macromolecules from the plasma solution to form a filtered plasma stream; and,
   e) combining said filtered plasma stream and said cellular stream to form a processed plasma stream.

17. The method of claim 16 wherein said process stream plasma is cooled before it is combined with said cellular element stream.

18. The method of claim 16, wherein said plasma solution is a human plasma solution.

19. The method of claim 16, wherein said plasma solution is a canine plasma solution.

20. An apparatus for removing selective macromolecules from a plasma solution comprising:
   a) a means for dividing a plasma containing solution containing macromolecules into a concentrated cellular element stream and a plasma stream;
   b) means for heating said plasma stream to a temperature which provides for the selective separation of the undesired macromolecules from the plasma solution while maintaining the levels of the desired macromolecules due to differences in the sieving coefficients of the macromolecules at the higher heated temperature;
   c) a means for filtering said heated plasma stream to selectively remove macromolecules; and,
   d) a means for combining said filtered plasma stream and said concentrated cellular element stream to form a processed stream substantially free of selective macromolecules.

* * * * *